United States Patent
Walsh

(10) Patent No.: US 12,364,807 B2
(45) Date of Patent: *Jul. 22, 2025

(54) SYSTEM AND METHOD FOR MAXIMUM INSULIN PUMP BOLUS OVERRIDE

(71) Applicant: Tandem Diabetes Care, Inc., San Diego, CA (US)

(72) Inventor: John Walsh, San Diego, CA (US)

(73) Assignee: Tandem Diabetes Care, Inc., San Diego, CA (US)

(*) Notice: Subject to any disclaimer, the term of this patent is extended or adjusted under 35 U.S.C. 154(b) by 306 days.

This patent is subject to a terminal disclaimer.

(21) Appl. No.: 17/975,112

(22) Filed: Oct. 27, 2022

(65) Prior Publication Data

US 2023/0047136 A1 Feb. 16, 2023

Related U.S. Application Data

(63) Continuation of application No. 15/948,368, filed on Apr. 9, 2018, now Pat. No. 11,484,642, which is a
(Continued)

(51) Int. Cl.
*A61M 5/142* (2006.01)
*A61M 5/168* (2006.01)
(Continued)

(52) U.S. Cl.
CPC ........ *A61M 5/14244* (2013.01); *A61M 5/168* (2013.01); *A61M 5/1723* (2013.01);
(Continued)

(58) Field of Classification Search
CPC .............. A61M 5/14244; A61M 5/168; A61M 5/1723; A61M 2205/18; A61M 2205/3569; A61M 2205/3576; A61M 2205/502
See application file for complete search history.

(56) References Cited

U.S. PATENT DOCUMENTS

| 4,529,401 | A | 7/1985 | Leslie et al. |
| 4,731,051 | A | 3/1988 | Fischell |

(Continued)

FOREIGN PATENT DOCUMENTS

WO 2013184896 A1 12/2013

OTHER PUBLICATIONS

Communication dated May 15, 2020 for EP Application No. 14 774 4499.9, 6 pages.
(Continued)

*Primary Examiner* — Shefali D Patel
*Assistant Examiner* — William R Frehe
(74) *Attorney, Agent, or Firm* — Merchant & Gould P.C.

(57) ABSTRACT

An ambulatory infusion pump can include a maximum bolus override procedure. When a bolus amount greater than a maximum bolus amount is requested, the ambulatory infusion pump can provide an alert indicating that the bolus amount requested exceeds the maximum bolus amount. If a user confirms the request in response to the alert, the bolus amount can be delivered to the user. The bolus amount delivered in response to the confirmation can be a first portion of the bolus amount. A reminder can then be provided that a second portion of the bolus amount that is a remaining portion of the requested bolus amount was also requested. If a second confirmation is received in response to the alert, the second portion of the bolus amount can also be delivered to the user.

19 Claims, 5 Drawing Sheets

Related U.S. Application Data continuation of application No. 13/800,387, filed on Mar. 13, 2013, now Pat. No. 9,940,441.

(51) Int. Cl.
  *A61M 5/172* (2006.01)
  *G16H 20/17* (2018.01)
  *G16H 40/63* (2018.01)

(52) U.S. Cl.
  CPC ............. *G16H 20/17* (2018.01); *G16H 40/63* (2018.01); *A61M 2205/18* (2013.01); *A61M 2205/3569* (2013.01); *A61M 2205/3576* (2013.01); *A61M 2205/502* (2013.01)

(56) References Cited

U.S. PATENT DOCUMENTS

| | | |
|---|---|---|
| 6,687,546 B2 | 2/2004 | Lebel et al. |
| 6,758,810 B2 | 7/2004 | Lebel et al. |
| 6,811,533 B2 | 11/2004 | Lebel et al. |
| 6,813,519 B2 | 11/2004 | Lebel et al. |
| 6,981,967 B2 | 1/2006 | Massengale et al. |
| 6,999,854 B2 | 2/2006 | Roth |
| 7,008,413 B2 | 3/2006 | Kovach et al. |
| 7,024,245 B2 | 4/2006 | Lebel et al. |
| 7,347,819 B2 | 3/2008 | Lebel et al. |
| 7,369,635 B2 | 5/2008 | Spital et al. |
| 7,704,226 B2 | 4/2010 | Mueller, Jr. et al. |
| 7,806,854 B2 | 10/2010 | Damiano et al. |
| 7,941,200 B2 | 5/2011 | Weinert et al. |
| 8,234,128 B2 | 7/2012 | Martucci et al. |
| 8,287,495 B2 | 10/2012 | Michaud |
| 8,414,563 B2 | 4/2013 | Karmen et al. |
| 8,573,027 B2 | 11/2013 | Rosinko |
| 9,474,856 B2 | 10/2016 | Morales |
| 9,492,608 B2 | 11/2016 | Saint |
| 9,603,995 B2 | 3/2017 | Rosinko et al. |
| 9,737,656 B2 | 8/2017 | Rosinko |
| 9,940,441 B2 * | 4/2018 | Walsh .................... G16H 20/17 |
| 10,016,561 B2 | 7/2018 | Saint et al. |
| 2001/0037083 A1 | 11/2001 | Hartlaub et al. |
| 2003/0060765 A1 | 3/2003 | Campbell et al. |
| 2005/0020996 A1 | 1/2005 | Hartlaub et al. |
| 2005/0022274 A1 | 1/2005 | Campbell et al. |
| 2005/0137530 A1 | 6/2005 | Campbell et al. |
| 2007/0118405 A1 | 6/2007 | Campbell et al. |
| 2009/0005729 A1 | 1/2009 | Hendrixson |
| 2009/0043290 A1 | 2/2009 | Villegas et al. |
| 2009/0088731 A1 * | 4/2009 | Campbell ............... G16H 20/17 |
| | | 604/890.1 |
| 2010/0008795 A1 | 1/2010 | DiPerna |
| 2010/0057057 A1 | 3/2010 | Hayter |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0174553 A1 | 7/2010 | Kaufman et al. |
| 2010/0262434 A1 | 10/2010 | Shaya |
| 2010/0298685 A1 | 11/2010 | Hayter et al. |
| 2010/0305965 A1 | 12/2010 | Benjamin et al. |
| 2011/0004189 A1 | 1/2011 | Vaidya et al. |
| 2011/0021898 A1 | 1/2011 | Wei et al. |
| 2011/0040247 A1 | 2/2011 | Mandro et al. |
| 2011/0098548 A1 | 4/2011 | Budiman et al. |
| 2011/0106049 A1 | 5/2011 | Damiano et al. |
| 2011/0124996 A1 | 5/2011 | Reinke et al. |
| 2011/0130746 A1 | 6/2011 | Budiman |
| 2011/0152770 A1 | 6/2011 | DiPerna et al. |
| 2011/0184653 A1 | 7/2011 | Ray et al. |
| 2011/0224523 A1 | 9/2011 | Budiman |
| 2011/0320049 A1 | 12/2011 | Chossat et al. |
| 2012/0029468 A1 | 2/2012 | DiPerna et al. |
| 2012/0330227 A1 | 12/2012 | Budiman et al. |
| 2013/0053816 A1 | 2/2013 | DiPerna |
| 2013/0121630 A1 | 5/2013 | Blomquist |
| 2013/0283196 A1 | 10/2013 | Farnan et al. |
| 2013/0332874 A1 | 12/2013 | Rosinko et al. |
| 2014/0012511 A1 | 1/2014 | Mensinger et al. |
| 2014/0276420 A1 | 9/2014 | Rosinko |
| 2014/0276553 A1 | 9/2014 | Rosinko et al. |
| 2014/0276556 A1 | 9/2014 | Saint et al. |
| 2015/0182693 A1 | 7/2015 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0082188 A1 | 3/2016 | Blomquist et al. |
| 2016/0317743 A1 | 11/2016 | Estes |
| 2017/0165416 A1 | 6/2017 | Saint |
| 2017/0246380 A1 | 8/2017 | Rosinko et al. |
| 2018/0021514 A1 | 1/2018 | Rosinko |
| 2018/0133398 A1 | 5/2018 | Blomquist |

OTHER PUBLICATIONS

Application and File history for U.S. Appl. No. 13/800,387, filed Mar. 13, 2013. Inventors: Walsh et al.
Search Report dated Oct. 6, 2016 for EP Application No. 14774499.9, 10 pages.
Search Report and Written Opinion dated Jun. 9, 2014 for PCT Application No. PCT/US2014/018856 filed February 267, 2014, 12 pages.
Internation Search report and Written Opinion for PCT/US2014/018850 dated May 7, 2014.

* cited by examiner

SYSTEM AND METHOD FOR MAXIMUM INSULIN PUMP BOLUS OVERRIDE

RELATED APPLICATION

This application is a continuation of application Ser. No. 15/948,368, filed Apr. 9, 2018, which in turn is a continuation of application Ser. No. 13/800,387 filed Mar. 13, 2013, now U.S. Pat. No. 9,940,441, issued Apr. 10, 2018, all of which are hereby fully incorporated herein by reference.

FIELD OF THE INVENTION

The present invention is directed to pumps for the delivery of fluid, such as medicament including insulin, and, more particularly to providing users with the flexibility to override maximum bolus limits in pumps while still retaining the safety features of maximum bolus limits.

BACKGROUND

There are many applications in academic, industrial, and medical fields that benefit from devices and methods that are capable of accurately and controllably delivering fluids, such as liquids and gases that have a beneficial effect when administered in known and controlled quantities. Such devices and methods can be particularly useful in the medical field where treatments for many patients include the administration of a known amount of a substance at predetermined intervals.

Insulin-injecting pumps have been developed for the administration of insulin for those suffering from both type I and type II diabetes. Some insulin injecting pumps configured as portable infusion devices can provide continuous subcutaneous insulin injection and/or infusion therapy for the treatment of diabetes. Such therapy may include the regular and/or continuous injection or infusion of insulin into the skin of a person suffering from diabetes, and offers an alternative to multiple daily injections of insulin by an insulin syringe or an insulin pen. Such pumps can be ambulatory/portable infusion pumps that are worn by the user and that may use replaceable cartridges. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference.

Regulatory and other considerations require, e.g., that insulin pumps have a maximum bolus limit that may be defined as the maximum amount of insulin that a user can have the pump deliver at any one time. Many pumps also enable a user to set a customized maximum bolus amount that is less than such a limit programmed into the devices. This limit provides a safety feature that prevents a user from inadvertently taking a bolus that is much larger than necessary and potentially unsafe. For example, a user intending to take a bolus of 4 units of insulin may inadvertently enter 44 units of insulin, which could potentially cause serious health concerns for the user. Additionally, the highest level at which the maximum bolus limit can be set is typically the same for all users, even though each user's needs typically are different from one another. For example, there may be a patient for whom a bolus amount that is unsafe for much of the population would be perfectly acceptable, yet that patient's pump may have a programmed maximum bolus limit that will prevent the patient from taking such a bolus. In addition, there are circumstances where it may be appropriate for a user to receive a bolus of medicament such as insulin that is larger than the user's customized maximum bolus limit. For example, a user's blood sugar level might be much higher than normal, or the user might have consumed a much larger number of carbohydrates than usual. In such a circumstance, the user's custom-set limit will prevent the user from taking such a complete bolus, even if it is warranted.

Therefore, there is a need for a system and a method that provides for greater flexibility in establishing, maintaining and/or changing maximum bolus limits in fluid pumps for delivery of medicament such as insulin.

SUMMARY OF THE INVENTION

An ambulatory infusion pump can include a maximum bolus override procedure. When a bolus amount greater than a maximum bolus amount is requested, the pump can provide an alert indicating that the amount requested exceeds the maximum bolus amount. If the user confirms the request in response to the alert, the bolus amount can be delivered to the user. In some embodiments, following the confirmation a first portion of the bolus amount is delivered. A reminder is then provided that a second portion of the bolus amount that is a remaining portion of the requested bolus amount was also requested. If a second confirmation is received in response to the alert, the second portion of the bolus amount is also delivered to the user. In this manner, the pump provides the flexibility to override a maximum bolus limit while retaining safety benefits precluding accidental delivery of a larger than intended bolus.

In some embodiments, an ambulatory infusion pump includes a delivery mechanism adapted to facilitate delivery of medicament such as insulin to a user, a user interface, a memory and a processor. The memory can be adapted to store a maximum bolus limit defining a maximum bolus amount a user is allowed to enter by regulation or choice into the user interface for delivery by the delivery mechanism. The processor can be programmed to execute a bolus override procedure if a user requests a bolus greater than the maximum bolus limit. The bolus override procedure can include providing an alert indicating that the bolus amount requested exceeds the maximum bolus limit. If a confirmation of the request is received in response to the alert, the processor can cause the delivery mechanism to deliver the requested bolus. In some embodiments, a first portion of the bolus is delivered in response to the confirmation and then the processor provides one or more reminders that a second portion of the bolus that can be the remainder of the requested bolus amount was requested. In response to a second confirmation received in response to the reminder, the processor can cause the delivery mechanism to deliver the second portion of the bolus amount.

Certain embodiments are described further in the following description, examples, claims, and drawings. These embodiments will become more apparent from the following detailed description when taken in conjunction with the accompanying exemplary drawings.

DETAILED DESCRIPTION

Provided herein are systems, devices and methods for overriding a maximum bolus limit in an infusion pump and particularly in an insulin pump. Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1:
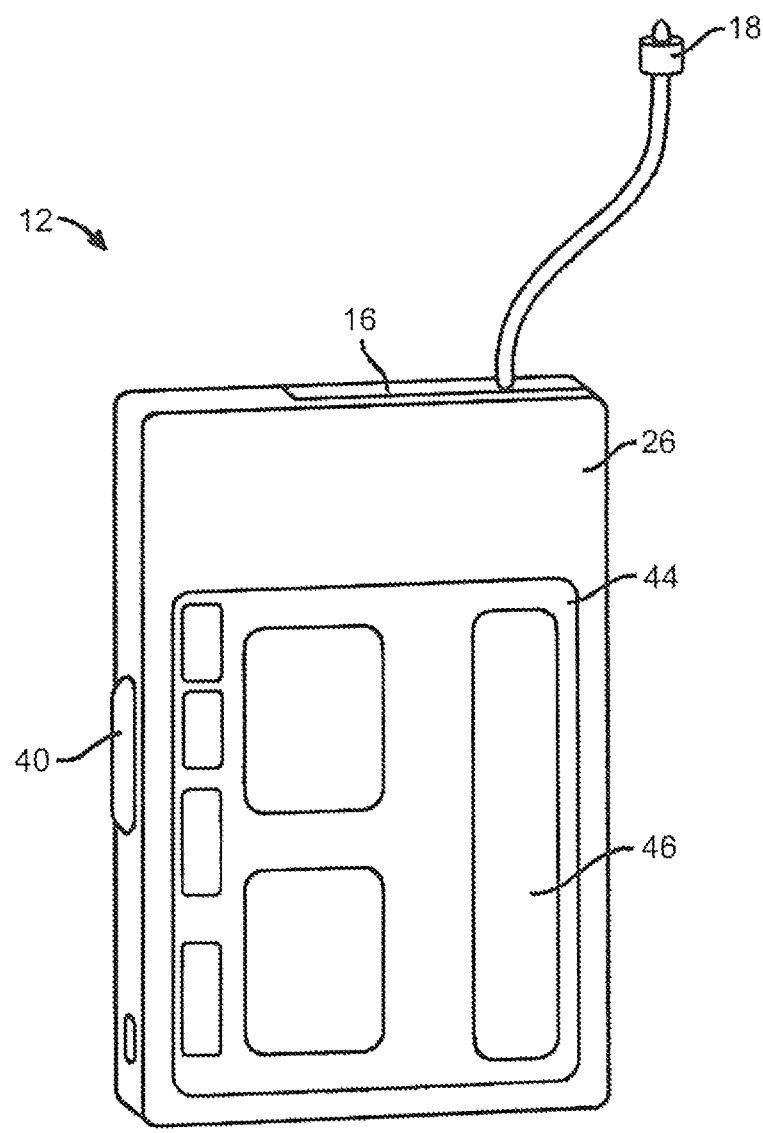
FIG. 1 is a perspective view of an infusion pump according to an embodiment of the present invention.

FIG. 1 depicts an embodiment of a pump 12 such as an infusion pump that can include an internal pumping or delivery mechanism and reservoir for delivering medicament such as insulin to a patient and an output/display 44. The type of output/display 44 may vary as may be useful for a particular application. The type of visual output/display may include LCD displays, LED displays, plasma displays, OLED displays and the like. The output/display 44 may also be an interactive or touch sensitive screen 46 having an input device such as, for example, a touch screen comprising a capacitive screen or a resistive screen. The pump 12 may additionally include a keyboard or other input device known in the art for data entry, which may be integrated with or separate from the display. The output/display 44 of the pump 12 may also include a capability to operatively couple to a secondary display device such as a laptop computer, mobile communication device such as a smartphone or personal digital assistant (PDA) or the like. Further details regarding such pump devices can be found in U.S. Patent Application No. 2011/0144586, which is incorporated herein by reference.

Figure 2:
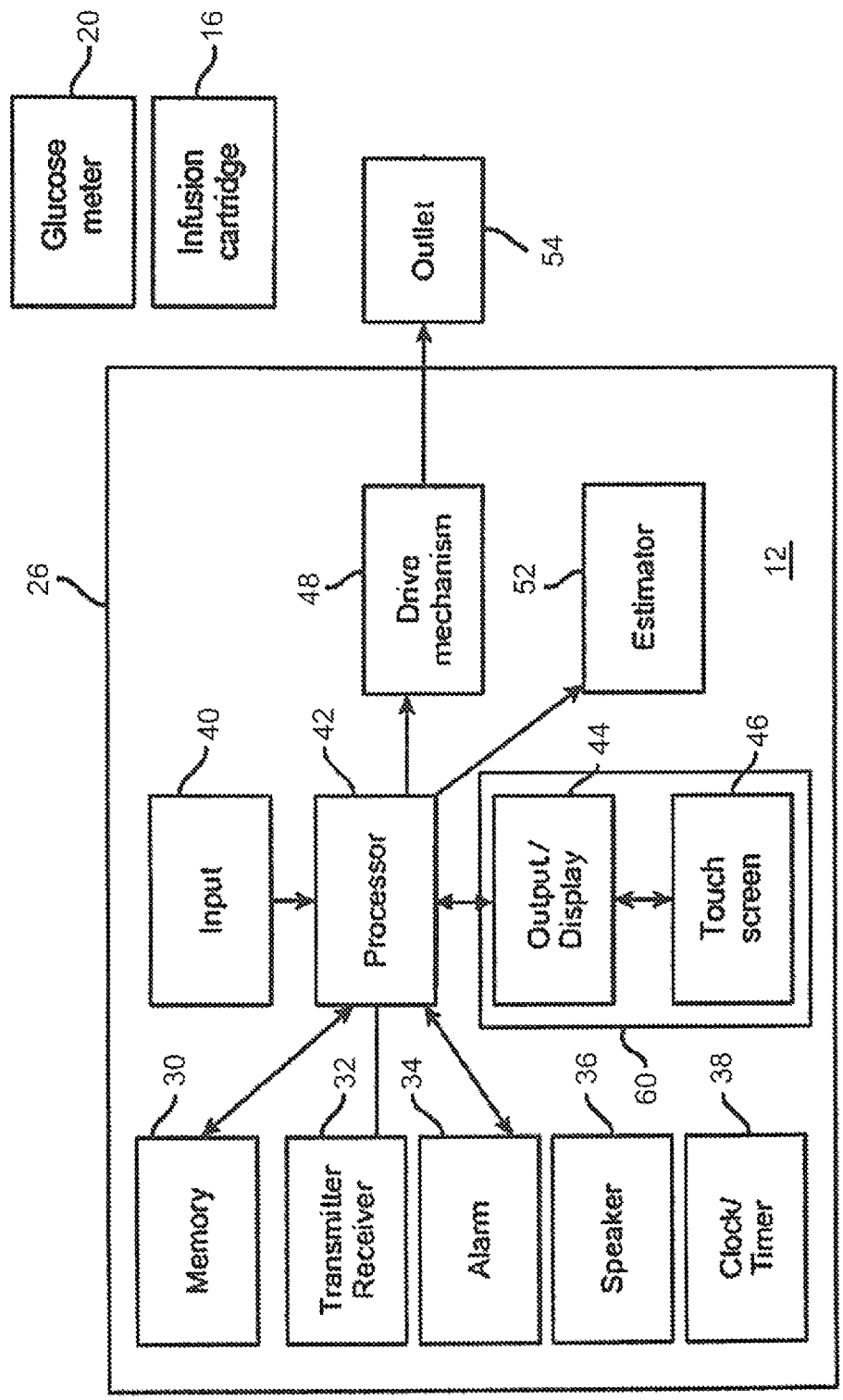
FIG. 2 is a block diagram representing an embodiment of an infusion pump.

FIG. 2 illustrates a block diagram of some of the features that may be incorporated within the housing 26 of the pump 12. The pump 12 includes a processor 42 that functions to control the overall functions of the device. The infusion pump 12 may also include a memory device 30, a transmitter/receiver 32, an alarm 34, a speaker 36, a clock/timer 38, an input device 40, the processor 42, a user interface suitable for accepting input and commands from a user such as a caregiver or patient, a drive mechanism 48, and an estimator device 52. One embodiment of a user interface as shown in FIG. 2 is a graphical user interface (GUI) 60 having a touch sensitive screen 46 with input capability. The memory device 30 may be coupled to the processor 42 to receive and store input data and to communicate that data to the processor 42. The input data may include user input data and non-user/sensor input data. The input data from the memory device 30 may be used to generate therapeutic parameters for the infusion pump 12. The GUI 60 may be configured for displaying a request for the user to input data and for receiving user input data in response to the request, and communicating that data to the memory.

The processor 42 may communicate with and/or otherwise control the drive mechanism, output/display, memory, a transmitter/receiver and other components. In some embodiments, the processor 42 may communicate with a processor of another device, for example, a continuous glucose monitor (CGM), through the transmitter/receiver. The processor 42 may include programming that can be run to control the infusion of insulin or other medicament from the cartridge, the data to be displayed by the display, the data to be transmitted via the transmitter, etc. The processor 42 may also include programming that may allow the processor to receive signals and/or other data from an input device, such as a sensor that may sense pressure, temperature, motion/activity or other parameters. The processor 42 may determine the capacity of the drug delivery reservoir and/or the volume of fluid disposed in the drug delivery reservoir and may set therapeutic parameters based on its determination.

The processor 42 may also include additional programming to allow the processor 42 to learn user preferences and/or user characteristics and/or user history data. This information can be utilized to implement changes in use, suggestions based on detected trends, such as, weight gain or loss. The processor can also include programming that allows the device to generate reports, such as reports based upon user history, compliance, trending, and/or other such data. Additionally, infusion pump device embodiments of the disclosure may include a "power off" or "suspend" function for suspending one or more functions of the device, such as, suspending a delivery protocol, and/or for powering off the device or the delivery mechanism thereof. For some embodiments, two or more processors may be used for controller functions of the infusion pump devices, including a high power controller and a low power controller used to maintain programming and pumping functions in low power mode, in order to save battery life.

The memory device 30 may be any type of memory capable of storing data and communicating that data to one or more other components of the device, such as the processor. The memory may be one or more of a Flash memory, SRAM, ROM, DRAM, RAM, EPROM and dynamic storage, for example. For instance, the memory may be coupled to the processor and configured to receive and store input data and/or store one or more template or generated delivery patterns. For example, the memory can be configured to store one or more personalized (e.g., user defined) delivery profiles, such as a profile based on a user's selection and/or grouping of various input factors, past generated delivery profiles, recommended delivery profiles, one or more traditional delivery profiles, e.g., square wave, dual wave, basal rate and bolus profiles, and/or the like. The memory can also store, for example, user information, history of use, glucose measurements, compliance and an accessible calendar of events.

The housing 26 of the pump 12 may be functionally associated with an interchangeable and a removable glucose meter 20 and/or infusion cartridge 16. The infusion cartridge 16 may have an outlet port 54 that may be connected to an infusion set (not shown) via an infusion set connector 18 or to an infusion and continuous glucose monitoring sensor combination. Further details regarding some embodiments of various infusion pump devices can be found in U.S. Patent Application No. 2011/0144586, which is hereby incorporated by reference.

Figure 3:
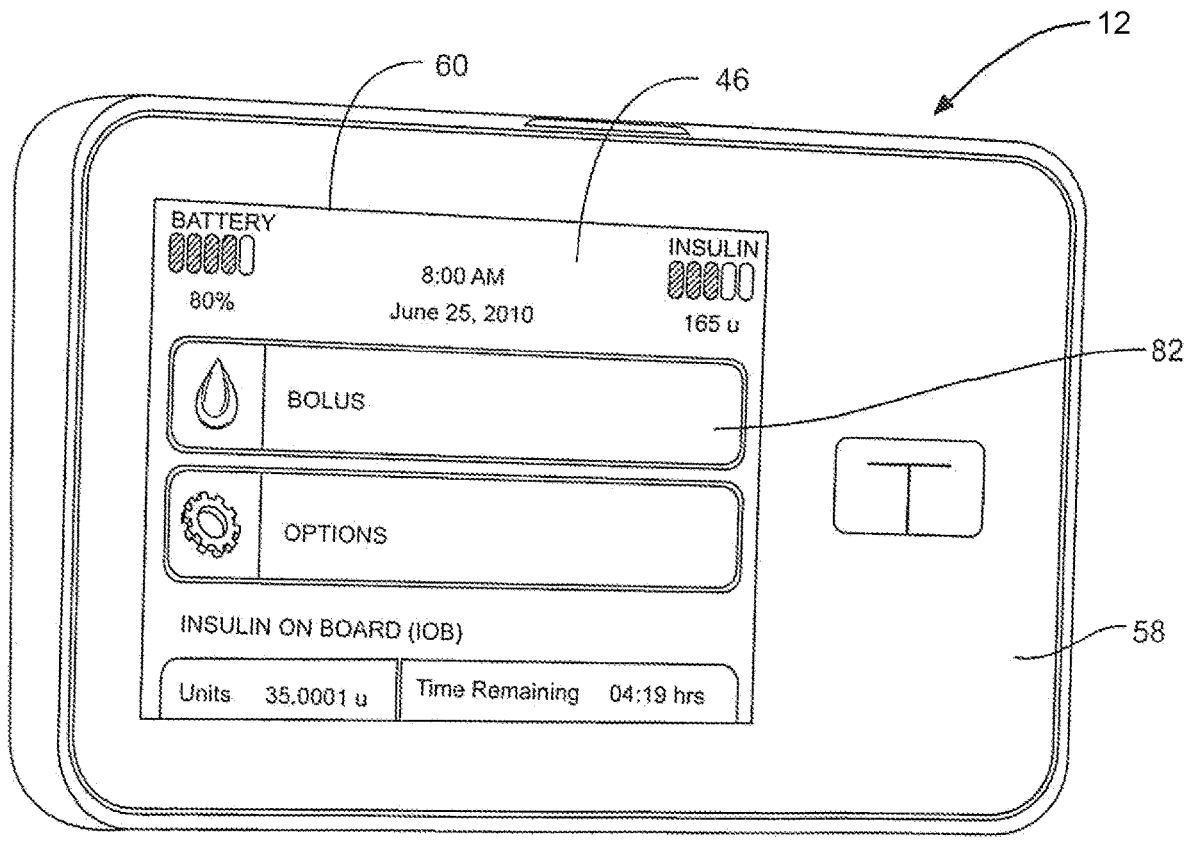
FIG. 3 depicts a screen shot of a home page screen of a graphical user interface of an infusion pump according to an embodiment of the present invention.

Referring to FIG. 3, a front view of the pump 12 is depicted. The pump 12 may include a user interface, such as, for example, a user-friendly GUI 60 on a front surface 58 or other convenient location of the pump 12. The GUI 60 may include a touch-sensitive screen 46 that may be configured for displaying data, facilitating data entry by a patient, providing visual tutorials, as well as other interface features that may be useful to the patient operating the pump 12. A bolus object 82 can also be displayed on the screen 46.

Figure 4:
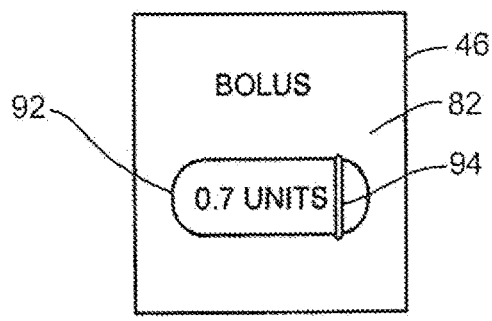
FIG. 4 depicts a screen shot of a bolus object of a graphical user interface of an infusion pump according to an embodiment of the present invention.

FIG. 4 illustrates an embodiment of a bolus object 82, which may be displayed on the touch screen 46. The bolus object 82 may be a "soft key" such that when selected by the user the processor initiates execution of a bolus delivery program that allows a user to set up the delivery of a bolus of medicament such as insulin. Furthermore, the bolus delivery program may include a bolus workflow or protocol which may, in combination with the processor 42 and memory 30 of the portable infusion device 12, present the user with pages or screen representations having one or more queries and/or information for setting up an appropriate bolus of medicament such as insulin to be delivered to the user.

In addition, once a bolus delivery has been setup, a bolus object 82 may also include a bolus status indicator 92 that provides feedback to the user regarding the programmed bolus delivery of insulin. For example, the status indicator 92 may provide feedback as to how much of the bolus has been delivered to the user. The bolus status indicator 92 may display the total bolus volume of insulin to be delivered (shown by way of example as 0.7 units). The bolus status indicator may also provide animated feedback, such as an animated indicator line 94 or bar that moves in a generally intuitive manner such that the status of the bolus delivery is generally understood by the user. Furthermore, feedback may be provided to a user for any number of reasons and may be portrayed to a user in various configurations, e.g., one or more blinking lights, color changes on the display 46, audible, tactile (e.g., vibratory) indications, etc.

For example, the animated indicator line 94 may travel from one side to the other of the bolus status indicator 92 as the bolus is delivered to the user. By way of further example, as the animated indicator line 94 moves, the color on one side of the animated indicator line 94 may be a different color than the other side such that it is generally intuitive to a user as to the status of the bolus delivery process. Therefore, the bolus status indicator 92 may provide efficient and user-friendly information that is easily accessible for a user to view and understand the status of insulin being delivered.

Infusion pump 12 may be configured to allow a user to set up a personal delivery profile including a number of queries, confirmations, and opportunities for a user to view and modify information regarding a delivery profile. An exemplary delivery profile that allows a user to customize the delivery of medicament such as insulin, based on a number of settings, over, e.g., a twenty-four hour period is described in U.S. Patent Application No. 2011/0144586.

Current infusion pumps typically allow for delivery of two infusion types—a basal rate and a bolus delivery. A basal rate typically delivers insulin at a constant rate over an extended period of time and is provided to maintain target glucose levels throughout the day when a user is not eating.

Boluses are delivered to counteract carbohydrates consumed at meal times to maintain target glucose levels. For a meal bolus, for example, the user may enter the amount of carbohydrates the user is about to ingest and the user's carbohydrate ratio (the volume of insulin programmed to be delivered for every particular number of carbohydrates predicted to be consumed by the user). Based on this information, the infusion pump will generate an estimate of a bolus amount of insulin to be delivered. If accepted by the user, e.g., by entering a command such as by depressing a button, touching an object on a touchscreen, etc., the then-current basal delivery mode is suspended and the bolus delivery is initiated.

In some embodiments, one of the customizable insulin delivery parameters that can be set in the personal delivery profile stored in the memory 30 is a maximum bolus amount. In addition, the maximum bolus amount itself may have a maximum value to which the device will allow it to be set. The maximum bolus amount limits the size of a bolus that a user can deliver in order to prevent the user from inadvertently receiving a bolus larger or much larger than is needed. Such a circumstance can arise as a result of, for example, a data entry or a typographical error (such as a user inadvertently requesting, e.g., a bolus of 44 units of insulin when meaning to program a delivery of a bolus of 4 units of insulin). The maximum bolus limit parameter, therefore, serves a safety function by preventing the user from receiving an overly large and unsafe bolus of medicament such as insulin.

However, circumstances can arise that can lead either to a user regularly requiring a bolus of medicament such as insulin that is larger than the pump's maximum allowed value or that is larger or much larger than the user's typical requirements and therefore over the user's set limit. To address such situations, pump 12 can in some embodiments be provided with a maximum bolus override feature. Such a feature can provide the safety benefits of preventing inadvertent intake of a potentially unsafe amount of insulin while allowing the flexibility to take a larger than normal dose if appropriate for the given situation.

Figure 5:
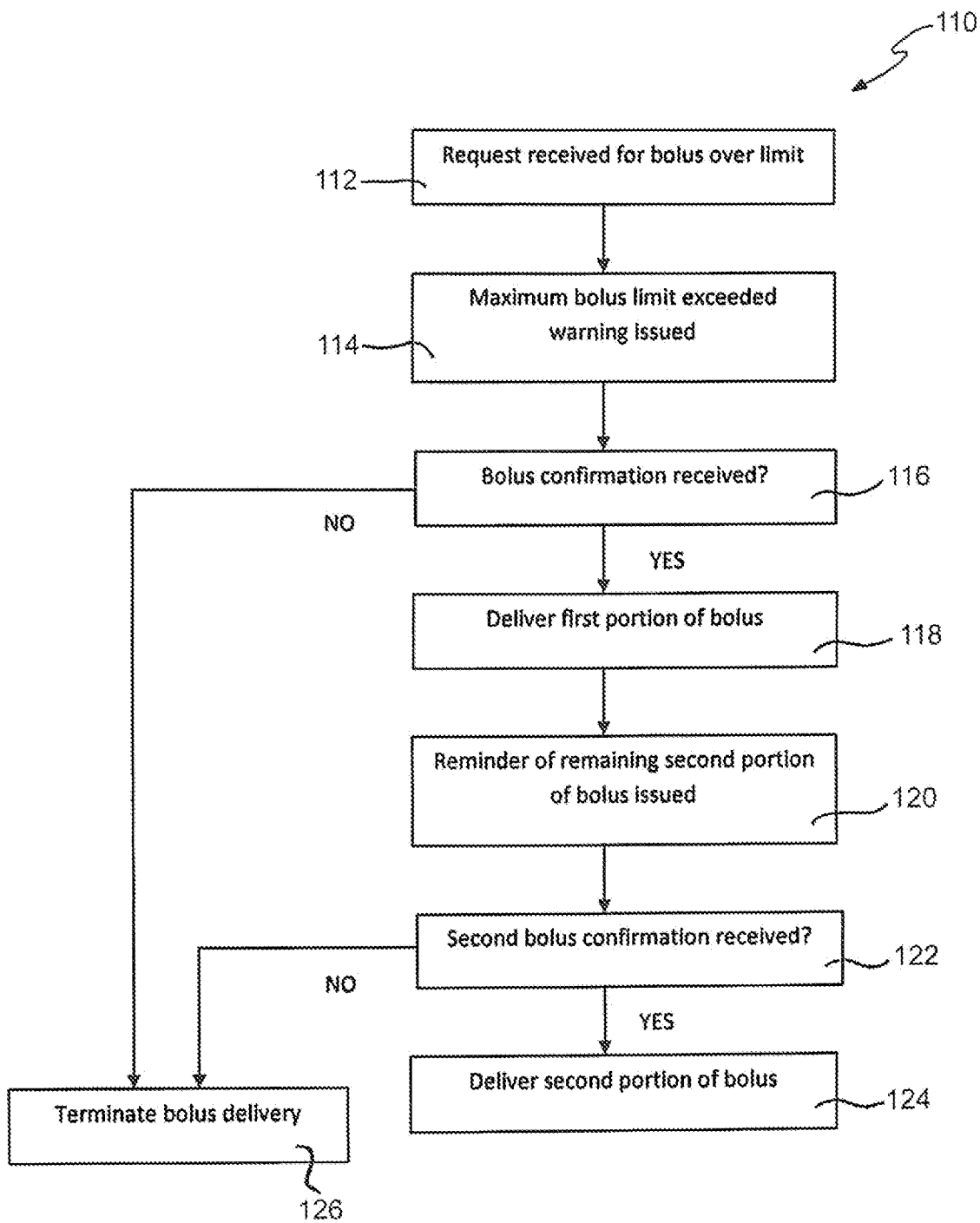
FIG. 5 is a flow diagram illustrating a maximum bolus override procedure according to an embodiment of the present invention.

FIG. 5 depicts a flowchart of a method for overriding a maximum bolus 110 in an insulin pump according to an embodiment of the invention. When the user programs or instructs delivery of a bolus of medicament that exceeds the maximum bolus limit set on the device at step 112 a warning alerting the user that the maximum bolus limit has been exceeded can be issued at step 114 (see, e.g., FIG. 6). The warning can include one or more of a visual alert displayed on the graphical user interface 60 and an audible or tactile alert. In one embodiment, a warning will be issued only if a maximum bolus override feature is turned on. Otherwise, the device will automatically not deliver the bolus and may alert the user that no bolus is being delivered. If the user does not confirm or cancels the bolus at step 116, the bolus delivery is terminated at step 126. If the user confirms the bolus, a first portion of the bolus is delivered to the user at step 118. The bolus can automatically be cancelled if the user does not respond to the warning within a predetermined amount of time. Alternatively, the first portion of the bolus can be automatically delivered if the user does not respond within the predetermined period of time.

In one embodiment, the first portion of the bolus is equal to the maximum bolus limit set on the device. In other embodiments, the first portion can be another amount, such as a predetermined percentage of the maximum bolus or a predetermined percentage of the requested bolus (so long as the remaining bolus amount is not over the maximum limit).

In further embodiments, the portion of the first bolus delivered immediately can be entered and/or adjusted by the user. These parameters can be programmed into the device by the user, or alternatively, can be preprogrammed into the device and modifiable by the user.

After the first portion of the bolus has been delivered, one or more reminders are displayed to the user at step 120 on the graphical user interface 60, which in some embodiments can be accompanied by an audible or tactile indication. In one embodiment, if a first reminder is not answered additional reminders can be given at escalating volumes, vibration levels, etc. in case the user is not noticing the reminders. If the user does not confirm or cancels the second portion of the bolus after the one or more reminders are given the bolus delivery is terminated at step 126. If the user does confirm the bolus, then at step 124 the remaining, second portion of the bolus is delivered to the user. As with the initial warning, the second portion of the bolus can in certain embodiments either automatically be delivered or automatically be cancelled if the reminder is not confirmed or cancelled within a predetermined period of time.

Figure 6:
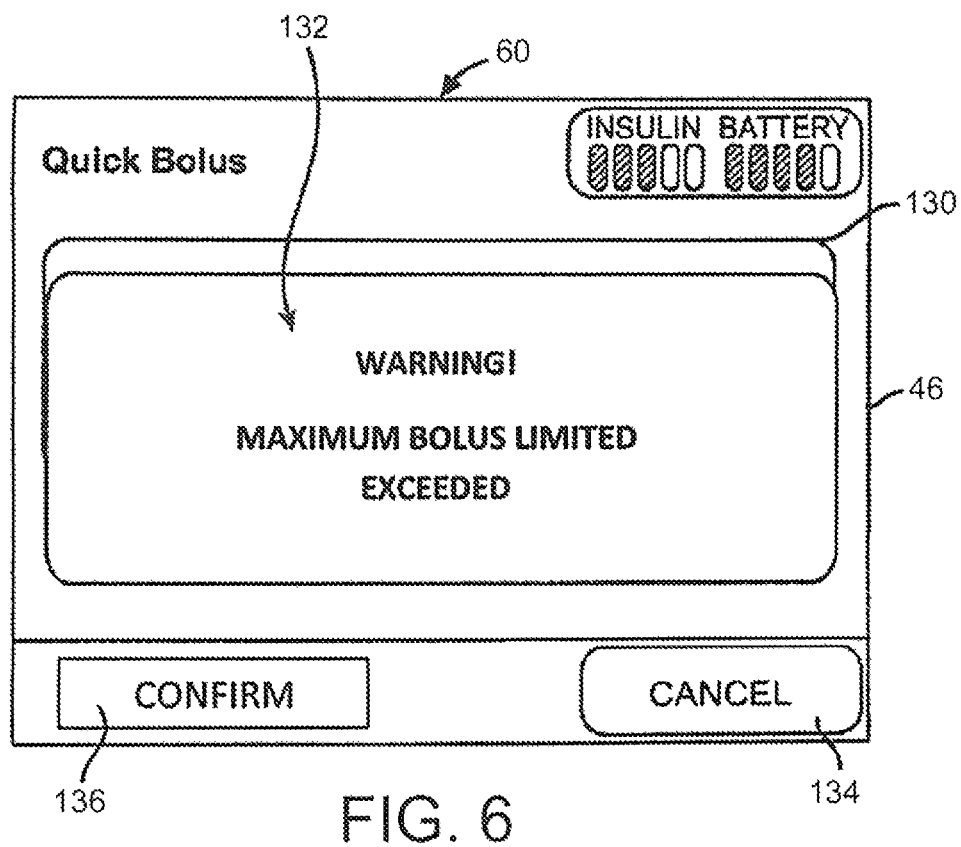
FIG. 6 is a screen shot of a maximum bolus limit warning screen according to an embodiment of the present invention.
Figure 7:
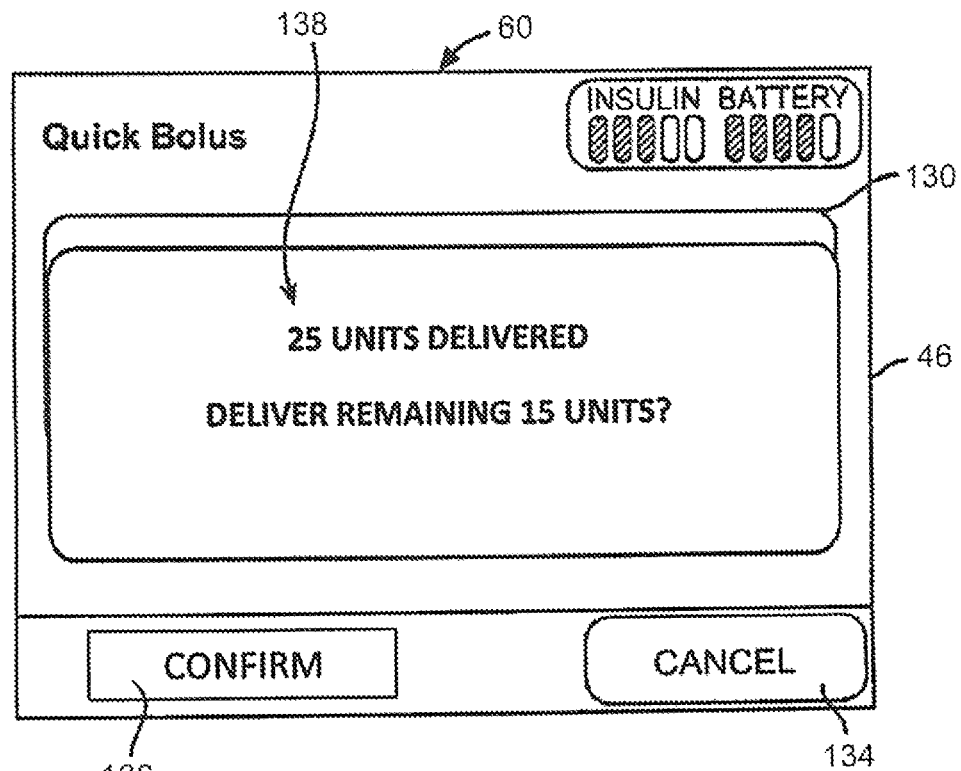
FIG. 7 is a screen shot of a bolus delivery reminder screen according to an embodiment of the present invention.

For example, if a user programs a bolus of 40 units of insulin but the maximum bolus limit on the device is 25 units, a warning screen 130 may be shown on the touch screen 46 of the graphical user interface 60 as shown in FIG. 6. The warning screen 130 can display a warning message 132 indicating that that maximum bolus limit has been exceeded and present the user with a selectable cancel object 134 and a selectable confirm object 136 to cancel or confirm the bolus delivery. If the user confirms delivery, as noted above a first portion of the requested bolus is delivered, such as the 25 units that is the maximum limit. Following delivery of the 25 units, the graphical user interface 60 will then display a reminder message 138 such as shown in FIG. 7. The reminder message 138 can identify the number of units delivered as well as the number of additional units requested. A cancel object 134 and a confirm object 136 provide the user with the ability to cancel or confirm the remaining insulin.

Thus, a maximum bolus override procedure as described herein provides flexibility to the user while preserving the safety benefits of the maximum bolus feature. Because the procedure requires the user to confirm the requested bolus initially and may also require a second confirmation to deliver additional units in a second portion of the bolus, the user is precluded from inadvertently taking an overly large bolus due to a typographical error or other mistake. However, the override confirmation provides the ability to deviate from the standard limits that may unduly restrict the delivery of boluses when large amounts are in fact warranted.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. An ambulatory infusion pump system, comprising:
   a delivery mechanism adapted to facilitate a delivery of insulin to a user;
   a user interface adapted to receive input data from the user;
   a memory adapted to store a maximum bolus limit defining a maximum bolus amount the user can operate a pump including the delivery mechanism to deliver at any one time; and
   at least one processor operably connected to the delivery mechanism, the user interface and the memory, the at least one processor adapted to execute a maximum bolus override procedure when the user manually enters a request for a delivery of a single, user-requested bolus amount greater than the maximum bolus limit through the user interface, the maximum bolus override procedure comprising:
   providing a first alert on the user interface warning the user that the single, user-requested bolus amount in the request exceeds the maximum bolus limit;
   receiving a first confirmation of the request in response to the first alert;
   causing the delivery mechanism to deliver a first portion of the single, user-requested bolus amount, the first portion being no more than the maximum bolus limit;
   after the first portion of the single, user-requested bolus amount is delivered to the user, providing a second alert on the user interface reminding the user that a second portion of the single, user-requested bolus amount comprising a remainder of the single, user-requested bolus amount was requested;
   receiving a second confirmation to deliver the second portion of the single, user-requested bolus amount; and
   causing the delivery mechanism to deliver the second portion of the single, user-requested bolus amount to the user in response to the second confirmation.

2. The ambulatory infusion pump system of claim 1, wherein the first portion of the single, user-requested bolus amount is equal to the maximum bolus limit.

3. The ambulatory infusion pump system of claim 1, wherein the first portion of the single, user-requested bolus amount is a predetermined percentage of the single, user-requested bolus amount.

4. The ambulatory infusion pump system of claim 1, wherein the user interface is adapted to enable the user to set the maximum bolus limit.

5. The ambulatory infusion pump system of claim 4, wherein the memory stores a maximum value for the maximum bolus limit, and the at least one processor is further adapted to inhibit the user from setting the maximum bolus limit above the maximum value.

6. The ambulatory infusion pump system of claim 1, wherein the first portion of the single, user-requested bolus amount is not delivered if the first confirmation is not received within a predetermined period of time.

7. The ambulatory infusion pump system of claim 1, wherein the first portion of the single, user-requested bolus amount is automatically delivered if the first confirmation is not received within a predetermined period of time.

8. The ambulatory infusion pump system of claim 1, wherein the second portion of the single, user-requested bolus amount is not delivered if the second confirmation is not received within a predetermined period of time.

9. The ambulatory infusion pump system of claim 1, wherein the first alert and the second alert each further include at least one of an audio alert and a tactile alert.

10. An ambulatory infusion pump system, comprising:
a delivery mechanism adapted to facilitate a delivery of insulin to a user;
a user interface adapted to receive input data from the user;
a memory adapted to store a maximum bolus limit defining a maximum bolus amount the user can operate a pump including the delivery mechanism to deliver at any one time; and
at least one processor operably connected to the delivery mechanism, the user interface and the memory, the at least one processor configured to:
provide a first alert on the user interface warning the user that a single, user-requested bolus amount in a request exceeds the maximum bolus limit;
receive a first confirmation of the request in response to the first alert through the user interface;
cause the delivery mechanism to deliver a first portion of the single, user-requested bolus amount to the user in response to the first confirmation, the first portion being no more than the maximum bolus limit;
after the first portion of the single, user-requested bolus amount is delivered to the user, provide a second alert on the user interface reminding the user that a second portion of the single, user-requested bolus amount comprising a remainder of the single, user-requested bolus amount was requested;
receive a second confirmation through the user interface to deliver the second portion of the single, user-requested bolus amount; and
cause the delivery mechanism to deliver the second portion of the single, user-requested bolus amount to the user in response to the second confirmation.

11. The ambulatory infusion pump system of claim 10, wherein the first portion of the single, user-requested bolus amount is equal to the maximum bolus limit.

12. The ambulatory infusion pump system of claim 10, wherein the first portion of the single, user-requested bolus amount is a predetermined percentage of the single, user-requested bolus amount.

13. The ambulatory infusion pump system of claim 10, wherein the user interface is adapted to permit the user to set the maximum bolus limit.

14. The ambulatory infusion pump system of claim 13, wherein the memory stores a maximum value for the maximum bolus limit, and the at least one processor is further adapted to inhibit the user from setting the maximum bolus limit above the maximum value.

15. The ambulatory infusion pump system of claim 10, wherein the first alert and the second alert each further include at least one of an audio alert and a tactile alert.

16. An ambulatory infusion pump system, comprising:
a delivery mechanism adapted to facilitate a delivery of insulin to a user;
a user interface adapted to receive input data from the user; and
at least one processor operably connected to the delivery mechanism and the user interface, the at least one processor configured to:
determine that an amount of a user programmed bolus is greater than a maximum bolus amount that the user is enabled to operate a pump including the delivery mechanism to deliver at any one time;
automatically divide the amount of the user programmed bolus into a first portion and a second portion, the first portion being no more than the maximum bolus amount;
deliver the first portion of the amount of the user programmed bolus to the user;
provide a reminder that the second portion of the amount of the user programmed bolus is remaining; and
deliver the second portion of the amount of the user programmed bolus to the user upon receiving a confirmation in response to the reminder.

17. The ambulatory infusion pump system of claim 16, wherein the first portion of the amount of the user programmed bolus is equal to the maximum bolus amount.

18. The ambulatory infusion pump system of claim 16, wherein the first portion of the amount of the user programmed bolus is a predetermined percentage of the amount of the user programmed bolus.

19. The ambulatory infusion pump system of claim 16, wherein the second portion of the amount of the user programmed bolus is not delivered if the confirmation is not received within a predetermined period of time.

* * * * *